(12) United States Patent
Hsu et al.

(10) Patent No.: US 7,544,712 B1
(45) Date of Patent: Jun. 9, 2009

(54) TREATMENT OF CORONAVIRUS INFECTION

(75) Inventors: Tsu-An Hsu, Taipei (TW); Hsing-Pang Hsieh, Taipei (TW); Yu-Sheng Chao, Taipei (TW); Chi-Min Chen, Hsinchu (TW); Jia-Tsrong Jan, Taipei (TW); Hwan-Wun Liu, Taipei (TW)

(73) Assignee: National Health Research Insitutes, Miaoli County (TW)

( * ) Notice: Subject to any disclaimer, the term of this patent is extended or adjusted under 35 U.S.C. 154(b) by 868 days.

(21) Appl. No.: 10/856,281

(22) Filed: May 28, 2004

Related U.S. Application Data

(60) Provisional application No. 60/474,053, filed on May 28, 2003, provisional application No. 60/515,288, filed on Oct. 29, 2003.

(51) Int. Cl.
*A61K 31/33* (2006.01)
*A01N 47/10* (2006.01)

(52) U.S. Cl. .................................. 514/485; 424/204.1

(58) Field of Classification Search ................ 514/310, 514/485; 424/204.1
See application file for complete search history.

(56) References Cited

OTHER PUBLICATIONS

Firelli v. Alonso-Caplen, Replication and Morphogenesis of Avian Coronavirus in Vero cells and their inhibition by Monensin, 1984, Virus Research, Abstract.*
Salanueva, Inigo, Structural Maturation of the Transmissible Gastroenteritis Coronavirus, 1999, Journal of Virology, vol. 73, Issue 10, pp. 7952-7964.*
E. Cox, Effect of Chlorpromazine on Experimental Diarrhea in Just-Weaned Piglets, 1989, Journal of Veterinary Medicine, Series A, vol. 36, Abstract from HCAPLUS.*
Niclosamide Product Information, Jun. 1995, Drugs.com, pp. 1-5.*
Kathryn V. Holmes, SARS-Associated Coronavirus, May 2003, New England Journal of Medicine, vol. 348, pp. 1948-1951.*
Zachary A. Flake, MD et al., Practical Selection of Antiemetics, Mar. 1, 2004, American Family Physician, vol. 69, No. 5, pp. 1169-1174.*
Ksiazek et al., "A Novel Coronavirus Associated with Severe Acute Respiratory Syndrome", The New England Journal of Medicine, 348:1953-1966, 2003.

* cited by examiner

*Primary Examiner*—Mina Haghighatian
*Assistant Examiner*—Andriae M Holt
(74) *Attorney, Agent, or Firm*—Occhiuti Rohlicek & Tsao LLP

(57) ABSTRACT

A method for treating coronavirus infection by administering to a subject in need of the treatment an effective amount of one or more of the following compounds: aklavin, sanguinarine, amiodarone, chlorpromazine, clomiphene, dihydroergotamine, dipyridamole, emetine, ephedrine, prochlorperazine, promazine, propiomazine, aminacrine, fluphenazine, fenoterol, peruvoside, proglumide, atenolol, nerifolin, nefopam, cycloheximide, avermectin B1, bepridil, cinnarizine, ethisterone, pararosaniline, methylbenzethonium, niclosamide, pipobroman, homidium, calcimycin, anisomycin, metergoline, amodiaquine, danazol, danthron, ethopropazine, eucatropine, nortriptyline, resorcinol, mebhydrolin, mebeverine, trimipramine, triflupromazine, chlorprothixene, cyclobenzaprine, enoxacin, sulfanitran, monensin, nigericin, perphenazine, methoxamine, astemizole, trifluoperazine, acriflavinium, rotenone, acebutolol, quabain, methiothepin, convallatoxin, halcinonide, cyclosporin, pimethixene, mycophenolic acid, promethazine, mesoridazine, thioridazine, chlorprothixene, thiothixene, clozapine, haloperidol, haloperidol decanoate, loxapine, molindone, olanzapine, pimozide, quetiapine, risperidone, and amitriptyline.

9 Claims, No Drawings

TREATMENT OF CORONAVIRUS INFECTION

CROSS REFERENCE TO RELATED APPLICATIONS

Pursuant to 35 USC § 119(e), this application claims priority to U.S. Provisional Application Ser. No. 60/474,053, filed May 28, 2003, and U.S. Provisional Application Ser. No. 60/515,288, filed Oct. 29, 2003, the contents of which are incorporated herein by reference.

BACKGROUND

Coronavirus is believed to cause a large percentage of all common colds in adults, especially in winter and early spring. It was first isolated from chickens in 1937 by Beaudette and Hudson. In 1965, Tyrrell and Bynoe used cultures of human ciliated embryonic trachea to propagate the first human coronavirus in vitro.

Among the more than 30 strains isolated so far, three or four infect humans. For example, the severe acute respiratory syndrome, a newly emerging infectious disease, is associated with a novel coronavirus (Ksiazek et al., New England Journal Medicine, 2003, 348(20): 1953-1966). This life-threatening respiratory virus has caused worldwide outbreaks in 2003.

SUMMARY

This invention is based on the unexpected discovery that certain compounds are effective in treating a coronavirus infection.

Thus, in one aspect, this invention features a method for treating a coronavirus infection. The method includes administering to a subject in need of the treatment an effective amount of one or more of the following compounds (including their pharmaceutically acceptable salts and prodrugs): aklavin, sanguinarine, amiodarone, chlorpromazine, clomiphene, dihydroergotamine, dipyridamole, emetine, ephedrine, prochlorperazine, promazine, propiomazine, aminacrine, fluphenazine, fenoterol, peruvoside, proglumide, atenolol, nerifolin, nefopam, cycloheximide, avermectin B1, bepridil, cinnarizine, ethisterone, pararosaniline, methylbenzethonium, niclosamide, pipobroman, homidium, calcimycin, anisomycin, metergoline, amodiaquine, danazol, danthron, ethopropazine, eucatropine, nortriptyline, resorcinol, mebhydrolin, mebeverine, trimipramine, triflupromazine, chlorprothixene, cyclobenzaprine, enoxacin, sulfanitran, monensin, nigericin, perphenazine, methoxamine, astemizole, trifluoperazine, acriflavinium, rotenone, acebutolol, quabain, methiothepin, convallatoxin, halcinonide, cyclosporin, pimethixene, mycophenolic acid, promethazine, mesoridazine, thioridazine, chlorprothixene, thiothixene, clozapine, haloperidol, haloperidol decanoate, loxapine, molindone, olanzapine, pimozide, quetiapine, risperidone, or amitriptyline.

A subset of the compounds mentioned above are aklavin hydrochloride, sanguinarine sulfate, amiodarone hydrochloride, chlorpromazine, clomiphene citrate, dihydroergotamine mesylate, dipyridamole, emetine hydrochloride, ephedrine hydrochloride, prochlorperazine edisylate, promazine hydrochloride, propiomazine maleate, aminacrine, fluphenazine hydrochloride, fenoterol hydrobromide, peruvoside, proglumide, atenolol, nerifolin, nefopam, cycloheximide, avermectin B1, bepridil hydrochloride, cinnarizine, ethisterone, pararosaniline pamoate, methylbenzethonium chloride, niclosamide, pipobroman, homidium bromide, calcimycin, anisomycin, metergoline, amodiaquine dihydrochloride, danazol, danthron, ethopropazine hydrochloride, eucatropine hydrochloride, nortriptyline, resorcinol, mebhydrolin naphthalenesulfonate, mebeverine hydrochloride, trimipramine maleate, triflupromazine hydrochloride, chlorprothixene hydrochloride, cyclobenzaprine hydrochloride, enoxacin, sulfanitran, monensin sodium, nigericin sodium, perphenazine, methoxamine hydrochloride, astemizole, trifluoperazine hydrochloride, acriflavinium hydrochloride, rotenone, acebutolol hydrochloride, quabain, methiothepin maleate, convallatoxin, halcinonide, cyclosporin, pimethixene maleate, mycophenolic acid, promethazine, mesoridazine besylate, thioridazine hydrochloride, chlorprothixene, thiothixene hydrochloride, clozapine, haloperidol, haloperidol decanoate, loxapine succinate, molindone hydrochloride, olanzapine, pimozide, quetiapine fumarate, risperidone, and amitriptyline. Preferred compounds include prochloperazine edisylate, promazine hydrochloride, propiomazine maleate, cinnarizine, pararosaniline pamoate, calcimycin, clomiphene citrate, homidium bromide, chlorpromazine, triflupromazine hydrochloride, ethisterone, niclosamide, cyclobenzaprine hydrochloride, nortriptyline, mebhydrolin naphthalenesulfonate, monensin sodium, mebeverine hydrochloride, and danazol.

The above-described method can be used to treat, among others, porcine transmissible gastroenteritis virus infection and severe acute respiratory syndrome virus infection.

In another aspect, this invention features a packaged pharmaceutical product. The packaged product includes a container, one or more of the above-mentioned compounds in the container, and a legend (e.g., a label or an insert) associated with the container and indicating administration of the compound for treating coronavirus infection.

The compounds described above include the compounds themselves, as well as their salts and their prodrugs, if applicable. Such salts, for example, can be formed by interaction between a negatively charged substituent (e.g., carboxylate) on a compound and a cation. Suitable cations include, but are not limited to, sodium ion, potassium ion, magnesium ion, calcium ion, and an ammonium cation (e.g., teteramethylammonium ion). Likewise, a positively charged substituent (e.g., amino) can form a salt with a negatively charged counterion. Suitable counterions include, but are not limited to, chloride, bromide, iodide, sulfate, nitrate, phosphate, or acetate. Examples of prodrugs include esters and other pharmaceutically acceptable derivatives, which, upon administration to a subject, are capable of providing above compounds described above.

The compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

The details of the embodiments of the invention are set forth in the description below. Other features, objects, and advantages of the invention will be apparent from the following description and from the claims.

DETAILED DESCRIPTION

This invention relates to use of one or more compounds mentioned in the summary section above for treating coronavirus infection such as severe acute respiratory syndrome virus infection.

All of the compounds mentioned above are active ingredients of generic drugs readily available to the public. Some of them can be purchased from chemical companies, such as Sigma-Aldrich, St. Louis, Mo. Regimens for administering these drug compounds are well known and, if necessary, can be easily re-established. Effective doses will vary, as recognized by those skilled in the art, depending on the type or degree of the coronaviral infection; the subject's size, weight, age, and sex; the route of administration; the excipient usage; and the possible co-usage with other therapeutic treatment.

One aspect of this invention features a method of administering an effective amount of one or more of the above-mentioned compounds to a subject (e.g., a human or an animal, such as pig) for treating coronavirus infection. "Treating" refers to administering one or more above-described compounds to a subject, who has a coronavirus infection, a symptom of such an infection, or a predisposition toward such an infection, with the purpose to confer a therapeutic effect, e.g., to cure, relieve, alter, affect, ameliorate, or prevent the coronavirus infection, the symptom of it, or the predisposition toward it. Such a subject can be identified by a health care professional based on results from any suitable diagnostic method. "An effective amount" refers to the amount of one or more compounds described above that is required to confer a therapeutic effect on a treated subject.

To practice the method of the present invention, a composition having one or more of the above-mentioned compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions, and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active above-described compounds can also be administered in the form of suppositories for rectal administration.

A pharmaceutically acceptable carrier is routinely used with one or more active above-mentioned compounds. The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an above-mentioned compound. Examples of other carriers include colloidal silicon oxide, magnesium stearate, cellulose, sodium lauryl sulfate, and D&C Yellow #10.

The compounds mentioned in the summary section above can be preliminarily screened by in vitro assays for their efficacy against the replication of porcine transmissible gastroenteritis virus and the replication of severe acute respiratory syndrome virus (See Examples 1 and 2 below). Other methods will also be apparent to those of ordinary skill in the art. These compounds can be further screened by in vivo assays.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Swine testicle (ST) cells were grown in a 96-well plate in the presence of cell growth medium (MEM, supplemented with 100 units/mL penicillin, 100 μg/mL streptomycin, and 10% of gamma-irradiated fetal bovine serum). A virus stock was prepared by infecting ST cells with TFI-TGEV (a Taiwanese isolate of porcine transmissible gastroenteritis virus) and the virus titer (50% tissue culture infectious dose) was determined to be $10^{7.3}$/mL.

64 compounds mentioned in the summary section above were tested. For each test compound, a 10× solution was prepared as follows: in each well of a 96-well plate, 2 μL of a 1000× stock solution of a test compound was diluted in 198 μL of virus growth medium (MEM, supplemented with 100 units/mL penicillin, 100 μg/mL streptomycin, and 2% of gamma-irradiated fetal bovine serum).

When ST cells formed 80-90% confluence, cell growth medium was removed from each well. 180 μL of the virus growth medium and 20 μL of the 10× test compound solution were then added to each well. The final concentration for each drug, i.e., 10 μM, would be 1×, compared to its original concentration.

The plate was then incubated in a $CO_2$ incubator at 37° C. for 2 hours in the presence of a test compound. 50 μL of TFI-TGEV was then added to each well in a final concentration of 5 m.o.i. (multiplication of infection). After incubation in the $CO_2$ incubator at 37° C. for seven hours, the plate was inspected by an inverted microscope. Wells that showed cytopathic effect were marked. The supernatant in each well was then discarded. Each well was maintained in 200 μL of 80% acetone for 30 minutes.

The plate thus obtained was stained with immunofluorescent antibody as follows: A mixture of anti-TGEV MAb 40G8 ascites (anti-TFI nucleus protein monoclonal antibody, Animal Technology Institute, Taiwan) and 3-29 (anti-TFI surface protein monoclonal antibody, Animal Technology Institute, Taiwan) was diluted 1,000× in phosphate-buffered saline (PBS). 50 μL of the diluted antibody solution was then added to each well and the plate was subsequently incubated at 37° C. for one hour. The supernatant in each well was discarded and each well was washed three times by PBS. Fluorescein isothiocyanate conjugated goat anti-mouse IgG antibody (1,000× diluted) was added to each well. The plate was then incubated at 37° C. for another hour. Again, the supernatant in each well was discarded and each well was washed three times by PBS. After 50 μL of PBS was added to each well, the plate was inspected under an inverted fluorescence microscope.

TFI-TGEV replication was deemed completely inhibited if a well containing a drug showed no cytopathic effect before immunofluorescent antibody staining and no fluorescence (as compared to negative control) when examined under fluorescence microscopy. At least 95% of TFI-TGEV growth was deemed inhibited if there were no more than 20 green fluorescence cells in a well.

All of the 64 test compounds showed at least 95% inhibition of TFI-TGEV growth. Among them, 32 showed 100% inhibition of TFI-TGEV growth.

EXAMPLE 2

Vero E6 cells ($2 \times 10^4$/well) were grown in a 96-well plate with Dulbecco's modified Eagle's medium (DMEM) supplemented with 10% FBS for one day or until the cells grew to 80-90% confluence. The culture medium in each well was discarded and 100 μL of 2% FBS DMEM containing a 1:1,000 diluted drug solution was added to each well (3 wells for each drug), the final drug concentration being 10 μM. Three wells without drug treatment were used as cytopathic effect-positive control. The plate was incubated at 37° C. for 2 hours. Severe acute respiratory syndrome virus (Hong Kong) was inoculated into each well at a dose of 100 $TCID_{50}$/well, and the plate was kept in an incubator at 37° C. 72 hours after infection, the cytopathic morphology of the cells was inspected under an inverted microscope and the results were recorded.

51 compounds mentioned in the summary section above were tested. Unexpectedly, at least 16 of them were observed to inhibit the growth of the severe acute respiratory syndrome virus.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for treating coronavirus infection, comprising orally administering to a subject in need thereof an effective amount of niclosamide.

2. The method of claim 1, wherein the coronavirus infection is porcine transmissible gastroenteritis virus infection.

3. The method of claim 1, wherein the coronavirus infection is severe acute respiratory syndrome virus infection.

4. A method for treating coronavirus infection, comprising nasally administering to a subject in need thereof an effective amount of niclosamide.

5. The method of claim 4, wherein the coronavirus infection is porcine transmissible gastroenteritis virus infection.

6. The method of claim 4, wherein the coronavirus infection is severe acute respiratory syndrome virus infection.

7. A method for treating coronavirus infection, comprising parentally administering to a subject in need thereof an effective amount of niclosamide.

8. The method of claim 7, wherein the coronavirus infection is porcine transmissible gastroenteritis virus infection.

9. The method of claim 7, wherein the coronavirus infection is severe acute respiratory syndrome virus infection.

* * * * *